(12) United States Patent
Spence

(10) Patent No.: US 6,256,543 B1
(45) Date of Patent: Jul. 3, 2001

(54) TEMPORARY PACEMAKER LEAD

(76) Inventor: Paul A. Spence, 5818 Orion Rd., Louisville, KY (US) 40222

(*) Notice: Subject to any disclaimer, the term of this patent is extended or adjusted under 35 U.S.C. 154(b) by 0 days.

(21) Appl. No.: 09/312,785

(22) Filed: May 17, 1999

(51) Int. Cl.$^7$ .................................................. A61N 1/05
(52) U.S. Cl. ............................................................ 607/130
(58) Field of Search .................................... 607/119, 129, 607/130, 132

(56) References Cited

U.S. PATENT DOCUMENTS

| | | | |
|---|---|---|---|
| 4,010,756 | 3/1977 | DuMont et al. | 128/404 |
| 4,214,594 | 7/1980 | Little | 128/786 |
| 4,378,023 | 3/1983 | Trabucco | 128/785 |
| 4,630,617 | 12/1986 | Ritter et al. | 128/784 |
| 4,633,880 | 1/1987 | Osypka et al. | 128/642 |
| 5,089,015 | 2/1992 | Ross | 623/2 |
| 5,095,903 | 3/1992 | DeBellis | 128/419 |
| 5,217,027 | 6/1993 | Hermens | 128/784 |
| 5,350,419 | 9/1994 | Bendel et al. | 607/132 |
| 5,476,510 | 12/1995 | Eberhardt et al. | 623/2 |
| 5,782,901 | * 7/1998 | Praeger | 607/130 |
| 5,792,217 | 8/1998 | Camps et al. | 607/119 |
| 5,871,528 | 2/1999 | Camps et al. | 607/119 |
| 5,871,532 | 2/1999 | Schroeppel | 607/128 |

* cited by examiner

Primary Examiner—William E. Kamm
(74) Attorney, Agent, or Firm—Wood, Herron & Evans, L.L.P.

(57) ABSTRACT

A temporary pacemaker lead including a wire having an electrically conductive portion, a first connector portion on the wire, and an electrode having a second connector portion. The second connector portion is releasable engagement with the first connector portion so as to establish electrical conduction between the electrode and the electrically conductive portion of the wire. The electrode may be permanently affixed to the heart tissue and the wire may be easily released from and connected to the electrode.

7 Claims, 4 Drawing Sheets

TEMPORARY PACEMAKER LEAD

BACKGROUND OF THE INVENTION

Temporary pacing wires are placed at almost every cardiac operation, but there have been no advances for many years. There are a number of current temporary pacemaker leads available for pacing after cardiac surgery. Leads (in reality a bare segment of an insulated wire) can be attached to the heart by a suture which holds the exposed wire in contact with the surface of the heart. When the lead is removed it is simply pulled out, breaking the stitch. The other way to attach the temporary lead is to attach a needle to the end of it and then pass the needle through the heart with a partial thickness bight. The needle is then cut off the wire. Exposed wire is left in contact with the heart. The wire is removed by simply pulling it out. The wire often has a series of bends or a small amount of attached plastic material to increase the friction to keep it from coming out.

There are a number of problems with these two options. Referring to FIG. 1, the suture method requires that the surgeon place a stitch in the form of a loop 10 and then feed the wire 12 through the loop 10 and tie it. This is somewhat tedious, especially on a beating heart 14. The wire 12 under the suture loop to is often easily removed by even a minimum of pull on the wire and it frequently has to be replaced. When a secure wire 12 is removed, there is the risk that the surface of the heart 14 will be torn as the suture snaps or that the suture does not snap and a small divot 16 of myocardium is pulled off as also shown in FIG. 1. This can lead to bleeding which can be fatal.

The second system is shown in FIG. 2 whereby a wire suture 20 is passed through the heart 14 is quicker. The wire suture 20 must be passed and the wire cut off as shown at cut 22 located above a flared stop portion 24. Flared stop portion 24 is designed to prevent the wire from being pulled back through heart 14. However, during insertion the wire 20 frequently causes bleeding and the bleeders must be sutured. When the wire 20 is removed, there is a risk that the friction of the wire removal combined with the drag of the flared portion 24 will result in a piece of myocardium being torn, again resulting in bleeding. Also, the wire 20 frequently becomes dislodged before the chest is closed and it has to be replaced.

The prior art does not demonstrate the concept of leaving a small permanent electrode in place and separating this from the wire. This concept is very important because on removal the risk of bleeding comes when the wire is pulled through the heart muscle or when the suture must snap.

In short, current methods are somewhat tedious, can result in bleeding at insertion and removal and the leads frequently become dislodged requiring complete reinsertion. It would be very useful to ease the insertion, permit reattachment should the wire become dislodged and reduce the risk of bleeding when the wire is removed.

SUMMARY OF THE INVENTION

The invention contemplates a temporary pacing wire system which eliminates the risk of bleeding from the heart when the lead is attached. It is another object of this invention to demonstrate a temporary pacing lead which can be removed from the heart without the risk of bleeding from the heart. It is another object of this invention to demonstrate a temporary pacing lead which can be re-attached should it be inadvertently removed from the heart before the incision is closed. It is a further object of this invention to describe a temporary pacing system lead that can be quickly attached to the heart without need for suture.

An electrode is permanently attached to the heart. The electrode can be a very tiny piece of metal, such as a clip. Releasably attached to the electrode is a wire which can be removed from the electrode and reattached to it. The electrode does not cause bleeding on attachment to the heart. The electrode is not removed from the heart, so that when the wire is pulled there is no ripping of the heart tissue but only separation of the electrode from the wire. Should the wire be inadvertently removed from the electrode after it is attached it is possible to quickly reattach it.

The electrode could be sutured to the heart. More simply and more efficient would be a mechanically applied electrode clip. Clips can be applied in seconds and do not require suture. The clip could take the form of a current vessel ligation clip. Alternatively, specially modified clips for attachment could include an extension attached to a hemoclip which impales the heart. Another variation could include a clip that looks like a scorpion's pincer.

The attachment of the wire to the clip can be accomplished in a number of ways. The clip could have a small loop through which a loop of preformed pacing wire is attached. The loop on the pacing wire could open to ensure easy removal. The clip could have two parallel rabbit ear-like attachments for holding the wire in place. Many other attachments would be possible to configure.

There are multiple advantages to the invention. For example, no suturing is required with a clip-on electrode. The clip is attached by simply squeezing the handle of a small tool. The wire is preattached to the clip so that there is an instantly functioning pacemaker with no additional steps.

The pacing wire is attached reversibly to the electrode clip so that it can be easily pulled out without the risk of tearing myocardium. This is due to the fact that the clip is permanently attached to the heart and the wire slips away from or disengages the clip. There would be no direct dislodgement from the heart.

Should the wire become accidently dislodged during surgery, it can be easily reattached.

The product is easy to manufacture, package and distribute as it may take the form of existing hemoclip products.

Other advantages, objectives, and features of the invention will become more readily apparent to those of ordinary skill in the art upon review of the following detailed description taken in conjunction with the accompanying drawings.

DETAILED DESCRIPTION OF THE PREFERRED EMBODIMENT

Figure 1:
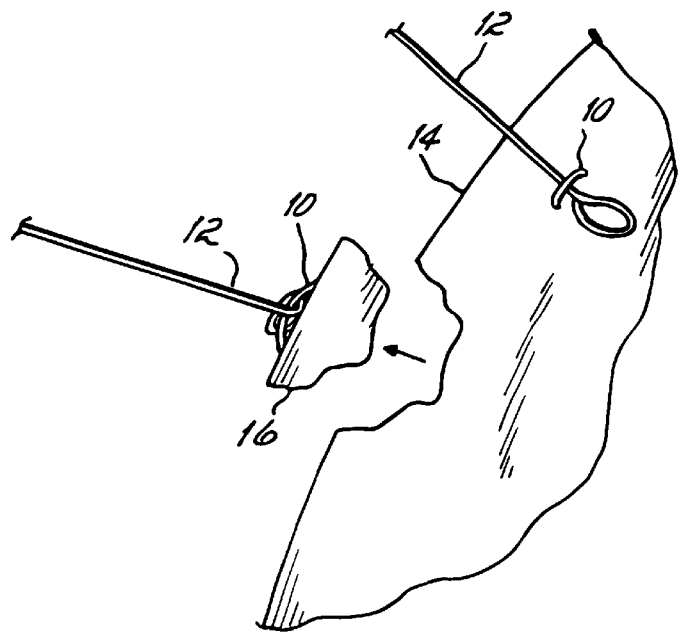
FIG. 1 is an elevational view showing a prior art method of attaching and removing a temporary pacing wire to the heart of a patient.
Figure 2:
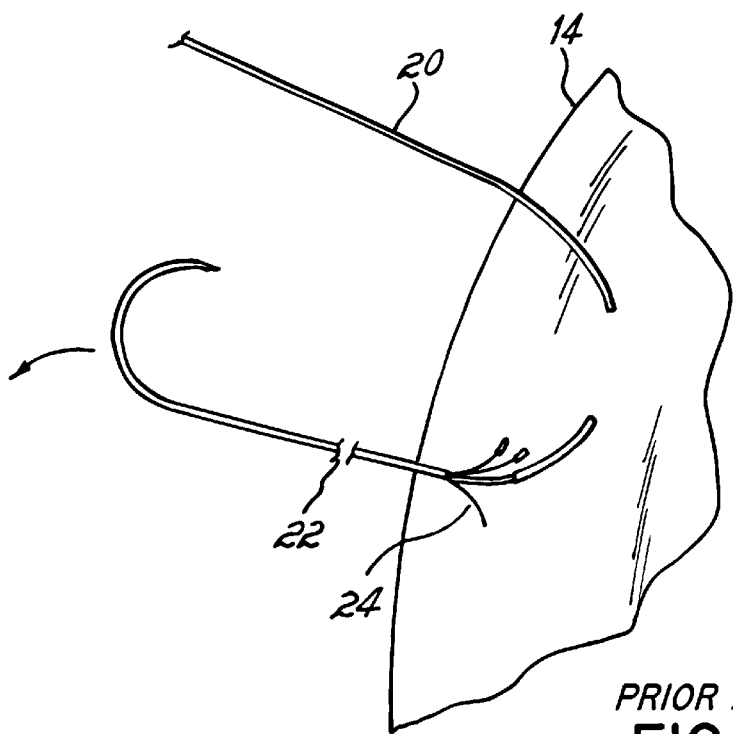
FIG. 2 is an elevational view similar to FIG. 1, but showing an alternative prior art method of attaching a temporary pacing wire to the heart.
Figure 3:
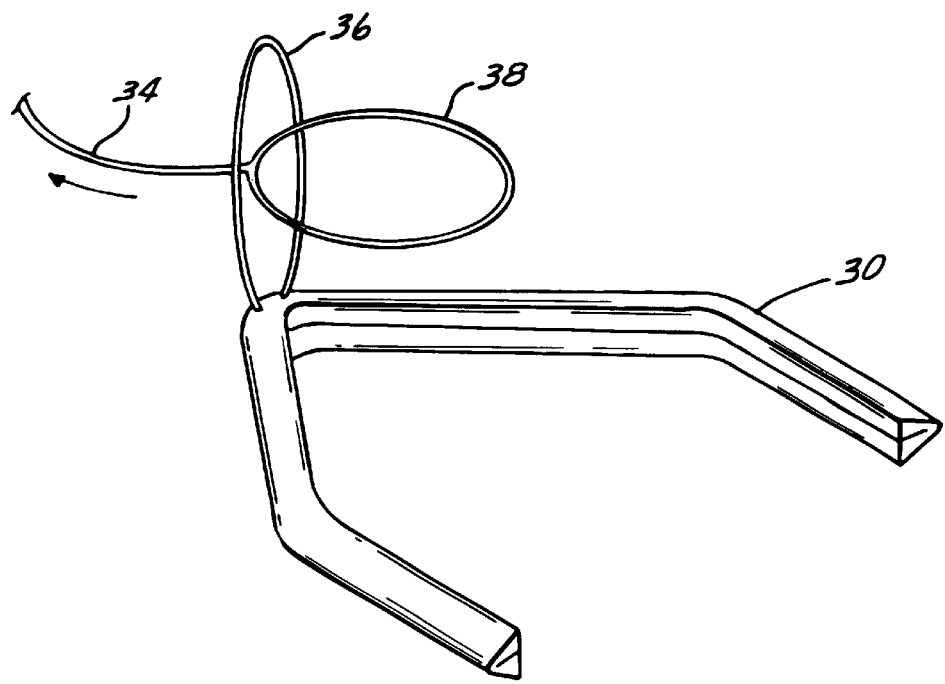
FIG. 3 is a perspective view of a temporary pacemaker lead constructed in accordance with one embodiment of the invention.
Figure 4:
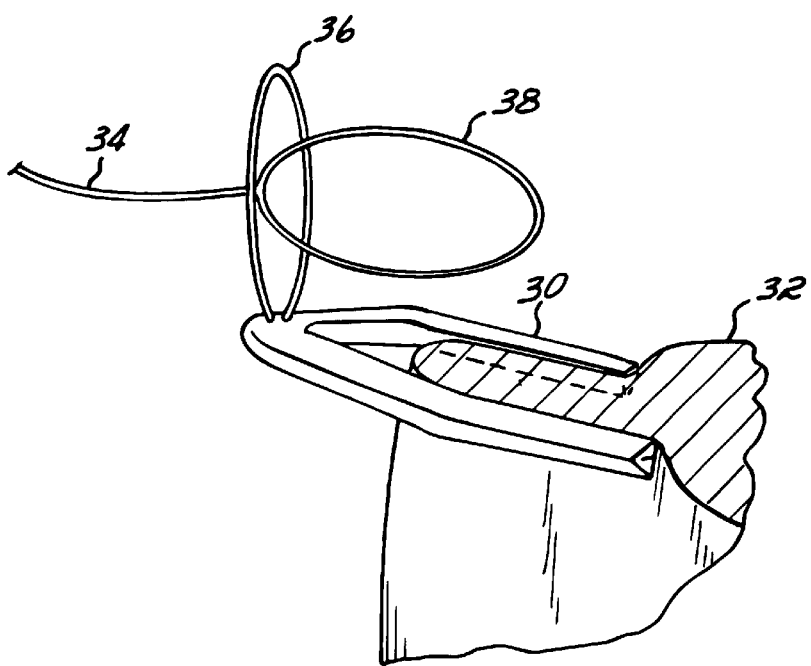
FIG. 4 is a perspective view showing the temporary pacemaker lead of FIG. 3 attached to the heart of a patient.

FIGS. 3 and 4 show a preferred embodiment of the invention. The electrode comprises a clip 30 which can be pinched onto the heart 32 (FIG. 4) for quick attachment with a clip applier. There will be no bleeding since there is no hole and tissue is merely pinched. The electrode 30 is attached to a wire 34 in a releasable manner. This may be accomplished with engageable and disengageable loops 36, 38 as shown. When the wire 34 is removed, the electrode stays on the heart and so there is no ripping of tissue.

Figure 5:
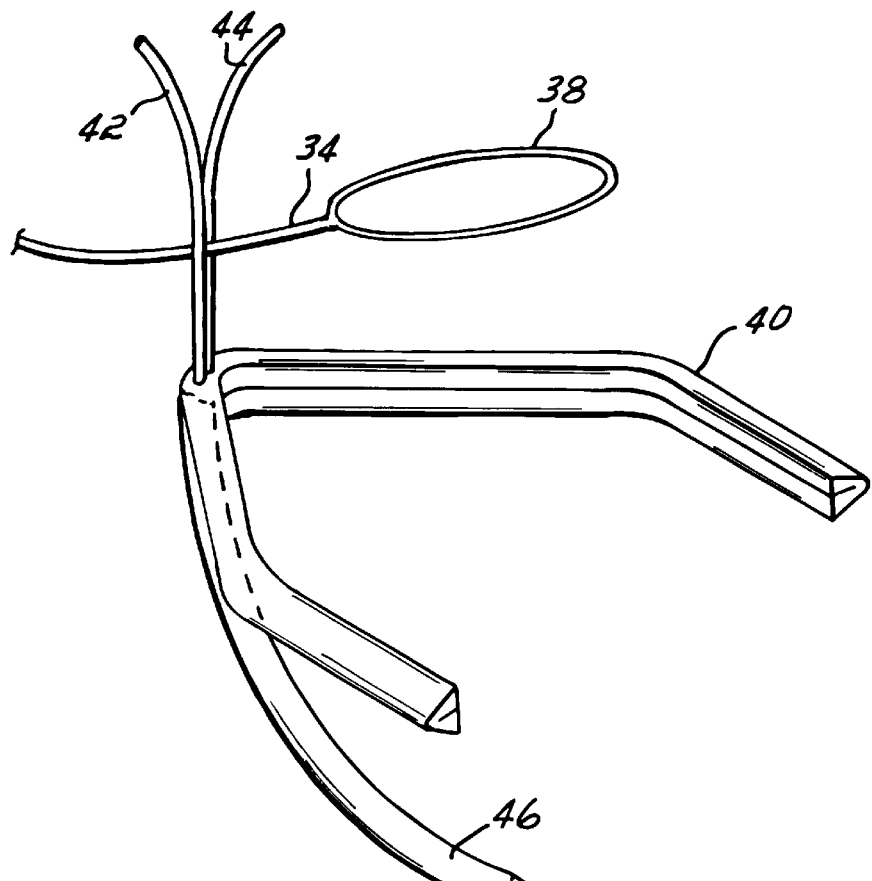
FIG. 5 is a perspective view of one alternative embodiment of the invention.
Figure 6:
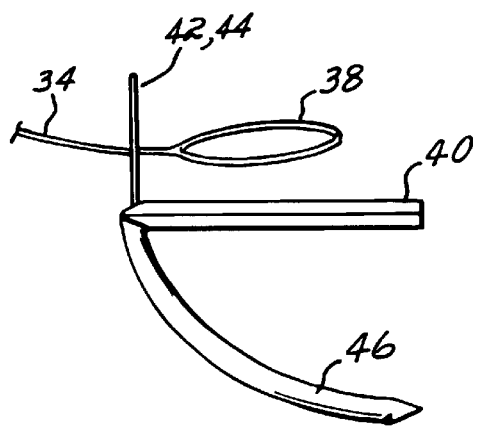
FIG. 6 is a side elevational view of the embodiment shown in FIG. 5.

FIGS. 5 and 6 show an alternate attachment of the wire 34 and an alternative electrode 40. This provides even less friction on removal. It is also easy to see that if the wire 34 comes free accidently during surgery, it would be very easy to reattach. This is because of the frictional engagement members 42, 44. FIGS. 5 and 6 also show an electrode variation as mentioned above. In this embodiment, there is a spike 46 that impales the heart which is then squeezed on with a clip applier as with the first embodiment. This assures better contact withe the heart muscle.

Figure 7:
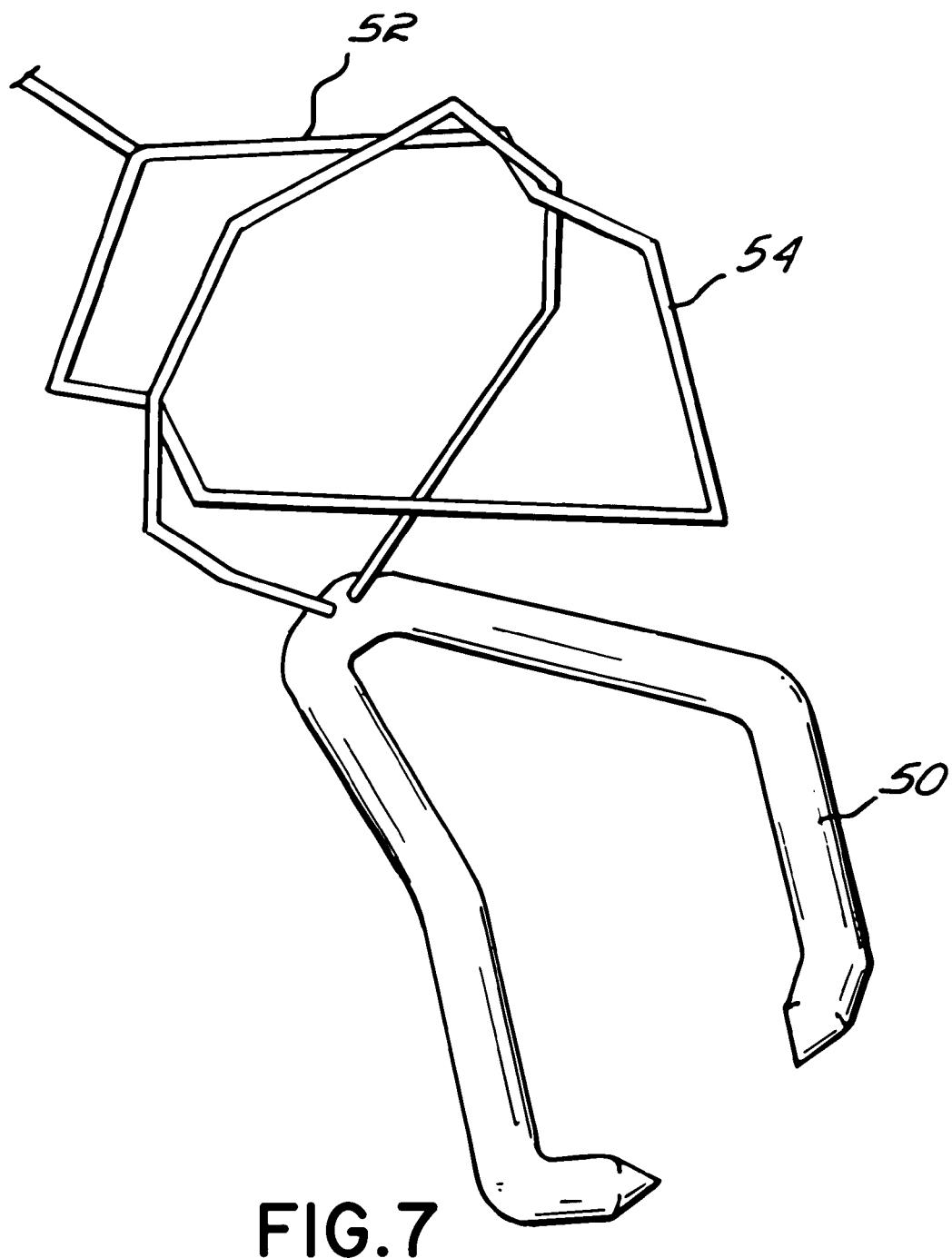
FIG. 7 is a perspective view of another alternative embodiment of the invention.

FIG. 7 shows another way to attach an electrode to the heart with a scorpion-type pincer 50 that is pinched with a clip applier. The sharp ends are squeezed together by the clip applier. Another alternative releasable electrode/wire link is shown. This again includes engageable and disengageable members 52, 54.

While the present invention has been illustrated by a description of a preferred embodiment and while this embodiment has been described in some detail, it is not the intention of the Applicants to restrict or in any way limit the scope of the appended claims to such detail. Additional advantages and modifications will readily appear to those skilled in the art. This has been a description of the present invention, along with the preferred methods of practicing the present invention as currently known. However, the invention itself should only be defined by the appended claims, Wherein I claim:

1. A temporary pacemaker lead for connection with heart tissue of a patient, the temporary pacemaker lead comprising:
   a wire having an electrically conductive portion;
   a first connector portion on the wire;
   an uninsulated metal electrode having a second connector portion releasably engaged with said first connector portion so as to establish electrical conduction between the electrode and the electrically conductive portion of the wire, whereby said electrode may be affixed to the heart tissue and said wire may be releasably secured to the electrode by way of the first and second connector portions.

2. A temporary pacemaker lead for connection with heart tissue of a patient, the temporary pacemaker lead comprising:
   a wire having an electrically conductive portion;
   a first connector portion on the wire;
   an electrode having a second connector portion releasably engaged with said first connector portion so as to establish electrical conduction between the electrode and the electrically conductive portion of the wire, whereby said electrode may be affixed to the heart tissue and said wire may be releasably secured to the electrode by way of the first and second connector portions;
   wherein said first and second connector portions comprise engageable and disengageable loops.

3. The temporary pacemaker lead of claim 1, wherein the connector portions each comprise frictionally engaging connector portions.

4. The temporary pacemaker lead of claim 3, wherein the second connector portion further comprises a pair of frictional engagement elements.

5. A temporary pacemaker lead for connection with heart tissue of a patient, the temporary pacemaker lead comprising:
   a wire having an electrically conductive portion;
   a first connector portion on the wire;
   an uninsulated metal electrode clip having a second connector portion releasably engaged with said first connector portion so as to establish electrical conduction between the electrode clip and the electrically conductive portion of the wire, said electrode clip having at least one movable portion allowing fixation of the clip to the heart tissue and wherein said wire may be releasably secured to the electrode clip by way of the first and second connector portions.

6. A temporary pacemaker lead for connection with heart tissue of a patient, the temporary pacemaker lead comprising:
   a wire having an electrically conductive portion;
   a first connector portion on the wire;
   an electrode having a second connector portion releasably engaged with said first connector portion so as to establish electrical conduction between the electrode and the electrically conductive portion of the wire, said electrode including a spike portion for insertion into the heart tissue and said wire may be releasably secured to the electrode by way of the first and second connector portions.

7. A temporary pacemaker lead for connection with heart tissue of a patient, the temporary pacemaker lead comprising:
   a wire having an electrically conductive portion;
   a first connector portion on the wire;
   an electrode having a second connector portion releasably engaged with said first connector portion so as to establish electrical conduction between the electrode and the electrically conductive portion of the wire, said electrode including a pair of spike portions adapted to be moved together into the heart tissue and said wire may be releasably secured to the electrode by way of the first and second connector portions.

* * * * *